United States Patent [19]

Bergstein et al.

[11] 4,356,324
[45] Oct. 26, 1982

[54] OPTICALLY ACTIVE 1,2-BIS-(DIPHENYLPHOSPHINE)-COMPOUNDS

[76] Inventors: Wolfgang Bergstein, Lindenstrasse 10, 6458 Rodenbach 1; Axel Kleemann, Greifenhagenstrasse 9, 6450 Hanau 9; Jurgen Martens, Hochstrasse 5, 8755 Alzenau, all of Fed. Rep. of Germany

[21] Appl. No.: 221,915

[22] Filed: Dec. 31, 1980

[30] Foreign Application Priority Data

Jan. 8, 1980 [DE] Fed. Rep. of Germany ....... 3000445

[51] Int. Cl.³ .............................................. C07F 9/50
[52] U.S. Cl. .................. 568/17; 252/431 P; 260/429 R
[58] Field of Search ......................................... 568/17

[56] References Cited

U.S. PATENT DOCUMENTS

| | | | |
|---|---|---|---|
| 3,849,480 | 11/1974 | Knowles et al. | 260/429 R X |
| 3,939,188 | 2/1976 | McVicker | 260/429 R |
| 3,949,000 | 4/1976 | Violet | 260/429 R X |
| 4,008,281 | 2/1977 | Knowles et al. | 260/429 R X |
| 4,119,652 | 10/1978 | Knowles et al. | 260/429 R |
| 4,166,824 | 9/1979 | Henderson | 568/17 |
| 4,201,714 | 5/1980 | Hughes | 260/429 R X |
| 4,294,989 | 10/1981 | Knowles et al. | 260/429 R X |

OTHER PUBLICATIONS

Brown et al., Tetrahedron Letters, No. 50, pp. 4859–4862 (1979).
Frysuk, Jour. Amer. Chem. Soc., vol. 100, Aug. 16, 1978, pp. 5491–5494.
King, Jour. Org. Chem., vol. 44, No. 10, pp. 1729–1731 (1979).

*Primary Examiner*—Helen M. S. Sneed
*Attorney, Agent, or Firm*—Cushman, Darby & Cushman

[57] ABSTRACT

The invention is directed to optically active 1,2-bis-(diphenylphosphino)-compounds of the general formula

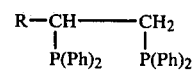

where Ph is a phenyl group and R is a straight or branched chain alkyl group with 2 to 20 carbon atoms or a benzyl group. Especially preferred are compounds in which R is an isopropyl or a benzyl group. These compounds can serve as chiral ligands in noble metal complexes, especially in rhodium complexes, which can be used as catalysts for the homogeneous asymmetrical hydrogenation of pro-chiral unsaturated compounds.

4 Claims, No Drawings

OPTICALLY ACTIVE 1,2-BIS-(DIPHENYLPHOSPHINE)-COMPOUNDS

BACKGROUND OF THE INVENTION

The invention is directed to new optically active 1,2-bis-(diphenyl-phosphino)-compounds, metal complexes which contain these as chiral ligands and the use of these metal complexes as catalysts for the homogeneous asymmetrical hydrogenation of unsubstituted or β-substituted 2-acylamido acrylic acid or their derivatives.

There are already known from Fryzuk, J. Amer. Chem. Soc. 100 (1978), pages 5491 to 5494 optically active 1,2-bis-(diphenylphosphino)-propane, a rhodium complexes containing these as chiral ligands and their use as catalysts for the homogeneous asymmetrical hydrogenation of unsubstituted or β-substituted 2-acylamido-acrylic acid and their derivatives. From King, J. Org. Chem. 44 (1979), pages 1729–1731, there are further known optically active 1,2-bis-(diphenyl-phosphino)-1-phenyl ethane, a rhodium complex containing these as chiral ligands and their use as catalyst for the homogeneous asymmetrical hydrogenation of 2-acylamido-cinnamic acid and their derivatives. (The entire disclosures of the Fryzuk and King articles are hereby incorporated by reference and relied upon). However, with the known rhodium complexes, there are only produced unsatisfactory optical yields in the asymmetrical hydrogenation.

SUMMARY OF THE INVENTION

Therefore, by the present invention, there should be solved the problem of improving the enantioselectivity in the homogeneous asymmetrical hydrogenation of unsubstituted or β-unsubstituted 2-acylamidoacrylic acid or its derivatives in the presence of metal complexes containing chiral ligand. The acyl group for example can be derived from a carboxylic acid and can be for example alkanoyl or aroyl.

According to the invention, therefore, there are prepared new optically active 1,2-bis-(diphenylphosphino)-compounds of the general formula

in which Ph is a phenyl group and R is a straight or branched chain alkyl group having 2 to 20 carbon atoms or is a benzyl group.

Particularly valuable are those compounds of formula (I) in which R is a straight or branched chain alkyl group having 2 to 10 carbon atoms, especially in isopropyl, isobutyl or secondary butyl group or a benzyl group.

Illustrative of compounds within the invention (both in the R form and in the S form) are 1,2-bis-(diphenylphosphino)-3-phenyl-propane;
1,2-bis-(diphenylphosphino)-3-methylbutane;
1,2-bis-(diphenylphosphino)-4-methylpentane;
1,2-bis-(diphenylphosphino)-3-methylpentane;
1,2-bis-(diphenylphosphino)-butane;
1,2-bis-(diphenylphosphino)-pentane;
1,2-bis-(diphenylphosphino)-octane;
1,2-bis-(diphenylphosphino)-decane;
1,2-bis-(diphenylphosphino)-dodecane;
1,2-bis-(diphenylphosphino)-tetradecane;
1,2-bis-(diphenylphosphino)-eicosane;
1,2-bis-(diphenylphosphino)-docosane.

The compounds of the invention of formula I can be produced in the following manner.

An optically active 2-hydroxycarboxylic acid of the general formula

in which R has the meaning given above is reduced as the free acid or as the ester (e.g. methyl or ethyl 2-hydroxy butyrate) in an ether, for example tetrahydrofuran, (or diethyl ether, dipropyl ether) under cooling with lithium-aluminum-hydride to the pure enantiomer-1,2-diol of the general formula

in which R again has the stated meaning. Thereby, there does not occur racemization. By reaction of this 1,2-diol with at least double the molar amount of p-toluenesulfonyl chloride under cooling in pyridine as solvent, there is obtained the corresponding 1,2-ditosylate. In this reaction also there does not occur racemization. The 1,2-ditosylalate formed is subsequently converted into the corresponding optically active 1,2-bis-(diphenylphosphino)-compound with at least the stoichiometric amount of an alkali metal diphenylphosphide (e.g. lithium sodium or potassium diphenylphosphide) in an ether, for example tetrahydrofuran, at a temperature between −20° and +25° C.

The thus obtained optically active compounds of formula (I) can serve as chiral ligands which contain as the central atom one of the platinum group of metals rhodium, iridium, ruthenium, osmium, palladium, or platinum.

Therefore, a further object of the invention is metal complexes which contain a platinum group metal as central atom and a compound of the invention of formula (I) as chiral ligands. Especially valuable are such metal complexes which contain rhodium as the central atom.

This type of rhodium complexes can be produced in situ by reaction of a compound of formula (I) with a complex of the general formula (II)

in which (en)$_2$ indicates two molecules of a monolefin such as ethylene, propylene, butylene, octene, hyclohexene or cyclooctene, or one molecule of a diolefin such as butadiene, isoprene, cyclooctadiene or norbornadiene and X is chlorine, bromine, or iodine in the molar ratio of 2:1 or with a complex of the general formula

in which (en)$_2$ is as defined above and Y is an acetonylacetate or a carboxylate group, for example an acetate, propionate butyrate, valerate or similar alkanoate or benzoate group, in the molar ratio 1:1. In this case, the reaction suitably takes place directly in the solvent in which later a hydrogenation should be undertaken in the presence of the rhodium complex formed, for example in methanol or ethanol.

Cationic rhodium complexes of the general formula

$$[Rh(en)_2A]^+Z^- \quad (IV),$$

in which (en)$_2$ again is defined as above and A is an optically active compound according to the invention of formula I and Z$^-$ is a tetrafluoroborate, hexafluorophosphate or perchlorate anion can be produced by the precedingly described reaction of a compound of formula (I) with a rhodium complex of formula (II) or (III) and subsequently adding an alkali metal (e.g. sodium or potassium) or silver salt of tetrafluoroboric acid, hexafluorophosphoric acid, or perchloric acid or of free perchloric acid. The reaction is suitably carried out in an alcohol such as methanol or ethanol. The salt or the free perchloric acid is suitably added in the form of the most highly concentrated aqueous solution possible. Thereby, it is not absolutely necessary that the compound of formula (I) be added in pure form. Rather, it can be employed also directly in the impure form obtained in its production, frequently as an oil, and the purification combined with the production of the cationic rhodium complex in one operating process. This can occur by reacting the rhodium complex of formula (II) or (III) with an equimolar (based on rhodium) amount of the impure compound of formula (I) in a lower alcohol (e.g. methanol or ethanol) as solvent, adding the salt or the free perchloric acid and subsequently precipitating out the impurities by adding water. Thereby, water is added, until the point where the complex solution, which has the characteristic orange-red color for the cationic rhodium complex, itself would be precipitate. Then the complex solution is separated from the precipitate formed and the complex recovered in solid form either through concentration of one solution or through further addition of water.

A further object of the invention is the use of the described rhodium complexes which contain a compound of formula (I) as chiral ligands as catalysts for the homogenous asymmetrical hydrogenation of unsubstituted or β-substituted α-acylamido acrylic acid or their derivatives.

As substrates for the asymmetrical hydrogenation, there can serve for example α-acylamido acrylic acids and their derivatives of the general formula

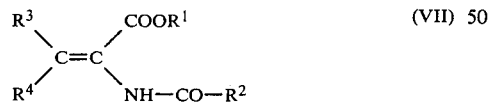

In this formula, R$^1$ indicates hydrogen, an alkali metal, e.g. sodium or potassium, or a lower alkyl group with 1 to 4 carbon atoms, e.g. methyl, ethyl, propyl, isopropyl, butyl or sec. butyl, preferably 1 to 2 carbon atoms and R$^2$ is a lower alkyl group with 1 to 4 carbon atoms, e.g. methyl, ethyl, propyl, isopropyl, butyl or sec. butyl, preferably 1 to 2 carbon atoms or a phenyl group, R$^3$ and R$^4$ can be the same or different and can be hydrogen, a straight or branched chain alkyl group with 1 to 10 carbon atoms, e.g. methyl, ethyl, propyl, isopropyl, butyl, isobutyl, sec. butyl, tert. butyl, amyl, hexyl, octyl or decyl, an unsubstituted phenyl group or a phenyl group substituted in the 3 and/or 4 position by hydroxyl, alkoxy, e.g. 1 to 4 carbon atom alkoxy such as methoxy, ethoxy, propoxy, butoxy isobutoxy, or acyloxy, e.g. acetoxy, propionoxy, butyroxy, benzoxy or an unsubstituted indolyl group or indolyl substituted in the 6-position by a methyl group or by chlorine.

Examples of such compounds include α-acetamido acrylic acid, sodium salt of α-acetamido acrylic acid, potassium salt of α-acetamido acrylic acid,
α-acetamido methyl acrylate,
α-acetamido ethyl acrylate,
α-acetamido butyl acrylate,
α-propionamido acrylic acid,
α-butyramido acrylic acid,
α-isobutyramido acrylic acid,
α-sec. butyramido acrylic acid,
α-benzamido acrylic acid,
α-formamido acrylic acid,
α-acetamido methacrylic acid,
α-acetamido crotonic acid,
α-acetamido pentenoic acid,
α-acetamido dodecenoic acid,
α-acetamido cinnamic acid,
sodium salt of α-acetamido cinnamic acid,
p-acetoxy α-acetamido cinnamic acid
p-acetoxy-m-methoxy α-acetamido cinnamic acid,
p-propionoxy α-acetamido cinnamic acid,
p-butyroxy α-acetamido cinnamic acid,
m-acetoxy α-acetamido cinnamic acid,
p-hydroxy α-acetamido cinnamic acid,
m-methoxy-α-acetamido cinnamic acid,
p-butoxy-α-acetamido-cinnamic acid,
m-hydroxy α-acetamido cinnamic acid,
α-acetamido indolyl acrylic acid,
α-acetamido-6-chloroindolyl acrylic acid,
α-acetamido-6-methylindolyl acrylic acid.

The mentioned prochiral substrates are changed by the asymmetrical hydrogenation into the corresponding optically active α-acylamidocarboxylic acids which can be saponified in known manner to the corresponding α-aminocarboxylic acids. If the optically active 1,2-bis-(diphenylphosphino)-compound of the invention contained in the rhodium complex used originally are produced from an L-α-hydroxycarboxylic acid, then, there is formed in a large excess the L-enantiomers of the optically active α-acylamidocarboxylic acid, on the contrary if the starting material is the corresponding D-α-acylamidocarboxylic acid, then there is formed the D-enantiomers in large excess. In both cases the desired enantiomers can be obtained optically nearly completely pure.

The hydrogenation takes place in the customary solvents for hydrogenation, such as alcohols, e.g. methanol, ethanol, propanol, isopropanol and ethers e.g. ethyl ether, propyl ether, tetrahydrofuran, or their mixture with aliphatic or aromatic hydrocarbons, e.g. hexane, octane, decane, xylene, benzene, toluene, or with water. The substrate concentration can extend from a 0.001 molar solution up to a supersaturated solution in the substrate. The hydrogen pressure can be between normal pressure and 50 bar, preferably between normal pressure and 25 bar, the reaction temperature between −20° and +50° C. Preferably, the hydrogenation is carried out at room temperature. The rhodium complex containing a compound of formula (I) as chiral ligands is suitably employed in such an amount that the molar ratio of substrate to catalysts is in the range between 1:1 and 50,000:1, preferably between 500:1 and 10,000:1.

Because of the sensitivity of the optically active 1,2-bis-(diphenylphosphino)-compounds of the invention and of the metal complexes containing them as chiral ligands to oxygen, it is suitable to carry out all reactions in a protective gas atmosphere, e.g. under nitrogen or argon and to store the respective reaction products under protective gas. Besides, it is advisable to also carry out the hydrogenation under anaerobic conditions.

In the hydrogenation of the prochiral substrates of formula (VII), there are obtained in all cases optically active N-acyl-α-amino carboxylic acids which readily can be changed via the corresponding optically active α-aminocarboxylic acids, into the corresponding optically active α-hydroxycarboxylic acids. Insofar as the prerequisites for the formulation of a hydrocarbon structure are given in the substrates to be hydrogenated, therefore, a part of the hydrogenation product can be detached for the production of new amounts of compounds of formula (I) and therewith new amounts of the metal complexes of the invention.

The invention will be further explained through the following examples, without limiting the extent of the invention.

The process can comprise, consist essentially of or consist of the stated steps with the materials set forth.

Unless otherwise indicated, parts are parts by weight.

EXAMPLE 1

Production of (R)-1,2-Bis-(diphenylphosphino)-3-phenyl-propane (a) (S)-1,2-Dihydroxy-3-phenyl-propane.

There were dropped into a suspension of 50 grams of LiAlH$_4$ in 750 ml of tetrahydrofuran (THF) cooled to 0° C. within 3 hours 83.1 grams of (S)-phenyl lactic acid dissolved in 250 ml of THF. The reaction mixture was boiled for 2 hours under reflux, after cooling treated portionwise with water and 43 ml of 4 N-NaOH and boiled for 0.5 hour under reflux. The white precipitate was filtered off and carefully washed with hot THF. The solvent was distilled off from the combined filtrates and the crude product fractionally distilled. There were obtained 64.6 grams of (S)-1,2-dihydroxy-3-phenyl-propane of boiling point 101°–102° C. (0.001 mbar).

$[\alpha]_D^{20} = -36°$ (c=1/EtOH)

| Elemental analysis: | % C | % H |
|---|---|---|
| Found: | 71,01 | 7,91 |
| Calculated: | 71,03 | 7,95 |

Yield: 85% of theory (b) (S)-3-Phenyl-propanediol-1,2-ditosylate 31.8 grams of the diol produced under (a) were dissolved in 20 ml of pyridine and in 0.75 hour dropped into a mixture of 83.9 grams of p-toluene-sulfonyl chloride and 105 ml of pyridine at 0° C. The mixture was further stirred overnight at room temperature and subsequently treated with 80 ml of ice water. Then the mixture was added to 400 ml of ice, which was treated with 100 ml of concentrated hydrochooric acid and the pasty crude product separated off with methylene chloride. The methylene chloride extract was first washed with dilute hydrochloric acid, then with water until at the neutral point. The solvent was distilled off. There remained 91 grams of crystalline (S)-3-phenyl-propanediol-1,2-tosylate.

Yield: 98,8% of Theory.

$[\alpha]_D^{20}$: $-26.6°$ (c=1/CHCl$_3$)

| Elemental analysis: | % C | % H | % S |
|---|---|---|---|
| Found: | 59,75 | 5,38 | 14,04 |
| Calculated: | 59,98 | 5,25 | 13,92 |

(c) (R)-1,2-Bis-(diphenylphosphino)-3-phenylpropane

There were dropped into 37.8 grams of sodium diphenyl phosphide, dissolved in 450 ml of THF at a temperature between −10° and −15° C., a THF solution of 25.7 grams of the ditosylate produced under (b). The precipitate falling out was filtered off and thoroughly washed with THF.

Half of the filtrate was stirred for one hour with 200 ml of water. After distilling off the THF in a vacuum, the oil produced was extracted with ether. The combined ether extractants were dried with Na$_2$SO$_4$. After distilling off the ether and drying the residue in a vacuum, there remained 12.3 grams of an oil which possessed a rotary value of $[\alpha]_D^{20}$: +45.91° (c=1,3634/CHCl$_3$).

| Elemental analysis: | % C | % H | % P |
|---|---|---|---|
| Found: | 81,08 | 6,26 | 12,56 |
| Calculated: | 81,13 | 6,19 | 12,68 |

$^{31}$P-NMR 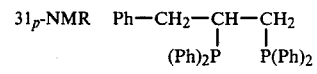

(b)    (a)

Chemical Displacement:
(a) δ= −4.9 ppm
(b) δ= −22.6 ppm
Coupling constant: J$_{P-P}$=31.1 Hz In accordance with $^{31}$P-NMR-Spectrum the product was 67%.

EXAMPLE 2

Production of (S)-1,2-Bis-(diphenylphosphino)-3-phenyl-propane (a) (R)-1,2-Dihydroxy-3-phenyl-propane Example 1 was repeated with the difference that in place of the (S)-phenyl lactic acid, there was employed (R)-phenyl lactic acid.

Yield of (R)-1,2-dihydroxy-3-phenyl propane: 84.5% of theory

| Elemental analysis: | % C | % H |
|---|---|---|
| Found: | 70,97 | 7,94 |
| Calculated: | 71,03 | 7,95 |

$[\alpha]_D^{20}$ = +35.8° (c=1/EtOH)

(b) (R)-3-Phenyl-1,2-propandiol-ditosylate

The diol produced under (a) was reacted in the manner stated in Example 1(b). Thereby, there was obtained (R)-3-phenyl-1,2-propanediol-ditosylate; Yield: 96.8% of theory

| Elemental analysis: | % C | % H | % S |
|---|---|---|---|
| Found: | 59,84 | 5,19 | 14,08 |
| Calculated: | 59,98 | 5,25 | 13,92 |

$[\alpha]_D^{20} = +26.3°$ (c=1/CHCl₃)

(c) (S)-1,2-Bis-(diphenylphosphino-3-phenylpropane

The (R)-3-phenyl-1,2-propanediol-ditosylate obtained under (b) was reacted in the manner described in Example 1(c) to form (S)-bis-1,2-(diphenylphosphino)-3-phenyl-propane.

| Elemental analysis: | % C | % H | % P |
|---|---|---|---|
| Found: | 81,28 | 6,27 | 12,81 |
| Calculated: | 81,13 | 6,19 | 12,68 |

$[\alpha]_D^{20} = -44.2°$ (c=1,2074/CHCl₃)

EXAMPLE 3

Production of (R)-1,2-Bis-(diphenylphosphino)-3-methyl-butane (a) (S)-1,2-Dihydroxy-3-methyl-butane 57.8 grams of (S)-2-hydroxy-isovaleric acid dissolved in 250 ml of THF were dropped in the course of 3 hours into a suspension of 46.4 grams of lithium-aluminum hydride in 700 ml of THF cooled to 0° C. The mixture was boiled under reflux for one hour, cooled and the excess LiAlH₄ destroyed by portionwise addition of water and dilute NaOH. The suspension was boiled again for a short time and the precipitate filtered off. This was washed with hot THF. The combined filtrates were freed from solvent on a rotary evaporator and the residue distilled in an oil pump vacuum. There were obtained 43.0 grams of (S)-1,2-dihydroxy-3-methylbutane boiling at 6° C. (0.5 mbar), corresponding to a yield of 84.5% of theory.

| Elemental analysis: | % C | % H |
|---|---|---|
| Found: | 57.76 | 11.80 |
| Calculated: | 57.66 | 11.61 |

Rotation: $[\alpha]_D^{20} = +9.9°$ (c=1/CHCl₃)

The NMR-spectrum corresponds to the product.

(b) (S)-3-Methyl-1,2-butandiol-ditosylate 165 grams of freshly recrystallized p-toluene sulfonyl chloride were suspended in 200 ml of pyridine, cooled to 0° C. and during one hour treated with a solution of 39.8 grams of the (S)-diol produced under (a) dissolved in 20 ml of pyridine. The mixture was stirred overnight. Subsequently, 160 ml of ice water were added and the mixture poured into 200 ml of concentrated hydrochloric acid in 800 ml of ice water. The product was extracted with a total of 600 ml of methylene chloride. The extract was washed with 0.5 N hydrochloric acid and subsequently with water until neutral, dried with Na₂SO₄ and freed from the solvent on the rotary evaporator. There remained 149 grams, corresponding to a yield of 94.3% of theory, of an oily residue which quickly crystallized. The rotary value of the (S)-3-methyl-1,2-butanediol ditosylate was $[\alpha]_D^{20} = -19.2°$ (c=4/EtOH)

| Elemental analysis: | % C | % H | % S |
|---|---|---|---|
| Found: | 55.31 | 5.89 | 15.32 |
| Calculated: | 55.32 | 5.86 | 15.54 |

The NMR-spectrum corresponded to the product.

(c) (R)-1,2-Bis-(diphenylphosphino)-3-methylbutane.

70.5 grams of sodium diphenylphosphide were dissolved in 400 ml of THF under argon, cooled to −20° C. and within 2 hours treated with a solution of 45.4 grams of the (S)-ditosylate produced under (b) in 150 ml of THF. The solution was then stirred for 3 hours at −5° C. and then stirred further overnight at room temperature. There were added 300 ml of oxygen free water, the THF distilled off under reduced pressure, and the aqueous phase extracted with ether. After distilling off the ether, the residue was taken up in warm ethanol, cooled and treated several times with ethanol until the diphosphane separated off in the form of colorless crystals. The crystalline (R)-1,2-Bis-(disphenylphosphino)-3-methyl-butane had a melting point of 76°–77° C. and a rotary value $[\alpha]_D^{20} = +98.1$ (c=0.626/CHCl₃)

| Elemental analysis: | % C | % H | % P |
|---|---|---|---|
| Found: | 78.89 | 7.00 | 14.12 |
| Calculated: | 79.07 | 6.87 | 14.06 |

The NMR-spectrum corresponds to the product.

EXAMPLE 4

Production of (S)-1,2-Bis-(diphenylphosphino)-3-methyl-butane (a) (R)-1,2-Dihydroxy-3-methyl-butane was produced analogous to the S-isomer (see Example 3(a)) starting from (R)-2-hydroxy-isovaleric acid. The yield was 86.5% of theory

| Elemental analysis: | % C | % H |
|---|---|---|
| Found: | 57.80 | 11.82 |
| Calculated: | 57.66 | 11.61 |

Rotary value $[\alpha]_D^{20} = -10.0°$ (c=1/CHCl₃)

(b) (R)-3-Methyl-1,2-butandiol-ditosylate was produced from (R)-1,2-dihydroxy-3-methyl-butane in a manner analogous to the S-isomer (see Example 3(b)). The yield was 87.8% of theory

| Elemental analysis: | % C | % H | % S |
|---|---|---|---|
| Found: | 55.48 | 5.90 | 15.56 |
| Calculated: | 55.32 | 5.86 | 15.54 |

Rotary value $[\alpha]_D^{20} = +19°$ (c=4/EtOH)

(c) (S)-1,2-Bis-(diphenylphosphino)-3-methyl-butane was produced from (R)-3-Methyl-1,2-butandiol-ditosylate analogous to the (R)-isomer (see Example 3(c)).

| Elemental analysis: | % C | % H | % P |
|---|---|---|---|
| Found: | 78.92 | 6.72 | 14.16 |
| Calculated: | 79.07 | 6.87 | 14.06 |

Rotary value $[\alpha]_D^{20} = -98.0°$ (c=0.630/CHCl₃)

EXAMPLE 5

Production of Cyclooctadiene-((R)-1,2-bis-(diphenylphosphino)-3-phenyl-propane)-Rhodium-tetrafluoroborate.

1.52 grams (which corresponds to 2.08 mmol of pure product) of the (R)-1,2-bis-(diphenylphosphino)-3-phenyl-propane produced according to Example 1(c) were dissolved in 100 ml of methanol, treated with 0.75 grams of solid [Rh (COD) Cl]$_2$ and stirred for 2.5 hours. 0.75 grams of NaBF$_4$ dissolved in 5 ml of water were slowly dropped in. After 2 hours, water was added until the precipitation of a dirty yellow precipitate was finished and the supernatant solution has taken on an orange-red color. The precipitate was separated off and further water added to the filtrate until no more precipitate came out. The orange-red precipitate was removed on a frit, washed with water and dried. There were obtained 1.2 grams of a complex, corresponding to a yield of 73% of theory.

| Elemental analysis: | % B | % C | % H | % F | % Rh | % P |
|---|---|---|---|---|---|---|
| Found: | 1.28 | 62.36 | 5.79 | 9.54 | 13.01 | 7.95 |
| Calculated: | 1.37 | 62.62 | 5.38 | 9.66 | 13.08 | 7.88 |

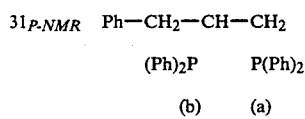

$31_{P\text{-}NMR}$   Ph—CH$_2$—CH—CH$_2$ (Ph)$_2$P      P(Ph)$_2$ (b)          (a)

| Chemical Shift: | Coupling Constants: |
|---|---|
| (a) δ = +42.5 ppm | $J_{P\text{-}Rh}$: 147.1 Hz |
| (b) δ = +55.9 ppm | $J_{P\text{-}Rh}$: 150.1 Hz |
|  | $J_{P\text{-}P}$: 31.7 Hz |

EXAMPLE 6

There were added to 54.6 ml of a saturated solution of α-acetamido cinnamic acid in two-parts of ethanol and one part of benzene by volume 10.89/10 ml A 23.6 mmol) 10.3 mg of the complex produced in Example 5 and the mixture sucked into an autoclave. There was applied 20 bar hydrogen pressure. After shaking for 1.5 hours at room temperature, the reaction was ended.

The reaction mixture was stirred for 15 minutes with 1.5 grams of a polystyrene acid ion exchange resin to remove the catalyst. After filtering off the ion exchange resin and distilling off the solvent under reduced pressure, 4.8 grams of N-acetyl-(S)-phenylalanine having the rotary value $[\alpha]_D^{20} = +46.8°$ (c=1/95% EtOH) can be isolated. Based on the literature known rotary value $[\alpha]_D^{20} = +47.5°$ (c=1/95% EtOH), this corresponds to an optical yield of 99% at a substrate: catalyst ratio of 1800:1.

EXAMPLE 7

11.15 grams of α-acetamido cinnamic acid in 125 ml of solvent (ethanol: benzene=2:1 by volume) were placed in a 250 ml flask and treated with 0.04 mmol of the catalyst produced in Example 5. Under stirring, hydrogen was led through the solution at room temperature. After 4 hours, the substrate was 64% hydrogenated. The rotary value of the dried product was $[\alpha]_D^{20} = +24°$ (c=1/95% EtOH).

EXAMPLE 8

50 grams of α-acetamido cinnamic acid were suspended in 250 ml of a 2:1 (by volume) mixture of ethanol and benzene, treated with 31.9 mg of the catalyst produced in Example 5, and hydrogenated at 15 bar in a 500 ml autoclave. After take up of the theoretical amount of hydrogen, the working up was as described in Example 6. There were isolated 49.8 grams of hydrogenated product with a rotary value of $[\alpha]_D^{20} = H+43.5°$ (c=1/95% EtOH) corresponding to an optical yield of 92% at a substrate-catalyst ratio of 6000:1

EXAMPLE 9

3.0 grams of α-acetamido acrylic acid were dissolved in 45 ml of a mixture of 2 parts by volume ethanol and 1 part by volume benzene and treated with 12.3 mg of the catalyst produced in Example 5. The reaction mixture was sucked into an evacuated 100 ml autoclave. It was pressurized with 14.8 bars of hydrogen pressure. After 2.5 hours, the theoretical amount of hydrogen was taken up. The 2.95 grams of N-acetyl-(S)-alanine worked up in the manner described in Example 6 had a rotary value $[\alpha]_D^{20} = 56.0°$ (c=2/water), corresponding to an optical yield of 84% based on the known rotary value $[\alpha]_D^{20} = 66.7°$ (c=2/H$_2$O) of the literature, at a substrate catalyst ratio of 1550:1.

EXAMPLE 10

3.7 grams of p-acetoxy-α-acetamido cinnamic acid were dissolved in 45 ml of absolute ethanol. There were added to the solution 6.75 mg of the catalyst produced in Example 5 and the reaction mixture sucked into an evacuated 100 ml autoclave. There were applied 21 bars of hydrogen pressure. After taking up of the theoretical amount of hydrogen it was worked up as customary (e.g. see Example 6). The isolated p-acetoxy-(S)-N-acetyl-phenyl-alanine had a rotary value $[\alpha]_D^{27} = +49.4°$ (c=1.CH$_3$OH), corresponding to an optical yield of 96% based on the known rotary value from the literature of $[\alpha]_D^{27} = +51.5°$ (c=1/CH$_3$OH).

EXAMPLE 11

4.4 grams of p-acetoxy-m-methoxy-α-acetamido cinnamic acid were dissolved in 45 ml of a mixture of 2 parts by volume of ethanol and 1 part by volume of benzene and treated with 12.9 mg of the catalyst produced in Example 5. The reaction mixture was sucked into a 100 ml autoclave. There were applied 14.9 bars hydrogen pressure. After 2.5 hours the theoretical amount of hydrogen was taken up. The product worked up as customary (e.g. see Example 6), 4.3 grams of p-acetoxy-m-methoxy-(S)-N-acetyl-phenyl-alanine had a rotary value $[\alpha]_D^{27} = +36.8°$ (c=1.CH$_3$OH), corresponding to an optical yield of 90.4%, based on the known rotary value from the literature of $[\alpha]_D^{27} = +40.7°$ (c=1/CH$_3$OH). No starting material was still detachable in the NMR spectrum.

EXAMPLE 12

Production of cyclo-octadiene-((S)-1,2-Bis-(diphenyl-phosphino)-3-phenyl-propane)-Rhodium-tetrafluoroborate Example 5 was repeated with the difference that in place of (R)-1,2-Bis-(diphenyl-phosphino)-3-phenyl-propane, the S-isomer was employed. The cyclo-octadiene-((S)-1,2-Bis-(diphenylphosphino)-3-phenyl-propane)-rhodium-tetrafluoroborate was obtained in a yield of 68% of theory.

| Elemental Analysis: | % B | % C | % H | % F | % Rh | % P |
| --- | --- | --- | --- | --- | --- | --- |
| Found | 1.30 | 62.42 | 5.63 | 9.75 | 13.17 | 8.08 |
| Calculated | 1.37 | 62.62 | 5.38 | 9.66 | 13.08 | 7.88 |

EXAMPLE 13

There were added saturated solution of α-acetamido cinnamic acid in a mixture of 2 parts by volume of ethanol and 1 part by volume of benzene 7.9 mg of the catalyst produced in Example 12. The reaction mixture was sucked into an evacuated 100 ml autoclave and pressurized with 17 bars of hydrogen pressure. After working up in the manner as described in Example 6, there were isolated 4.4 grams of N-acetyl-(R)-phenyl-alanine having a rotary value of $[\alpha]_D^{20} = -46.5°$ (c=1/95% EtOH), corresponding to an optical yield of 99%.

EXAMPLE 14

3.6 grams of p-acetoxy-α-acetamido cinnamic acid were dissolved in 45 ml of absolute ethanol. To this solution there were added 7.1 mg of the catalyst produced in Example 12. After sucking the reaction solution into an evacuated 100 ml autoclave it was pressurized with 20 bars hydrogen pressure. After taking up the theoretical amount of hydrogen, it was worked up as customary (e.g. as in Example 6). There were isolated 3.5 grams of p-acetoxy-N-acetyl-(R)-phenyl-alanine having a rotary value $[\alpha]_D^{27} = -48.4°$ (c=1.CH$_3$OH), corresponding to an optical yield of 94%.

EXAMPLE 15

Production in situ of the catalyst Cyclo-octadiene-((R)-1,2-bis-(diphenylphosphino)-3-methyl-butadiene)-Rhodium-acetylacetonate For the production of the catalyst there were dissolved in 10 ml of absolute alcohol at room temperature 0.1814 gram of the (R)-1,2-bis-(diphenylphosphino)-3-methyl-butane produced according to Example 3 and 0.1272 gram of cyclooctadiene-rhodium-acetylacetonate.

EXAMPLE 16

3.4 grams of α-acetamido-acrylic acid were dissolved in 75 ml of ethanol together with 0.5 ml of the catalyst solution of Example 15 in a 250 ml flash. Over a time of 6.5 hours hydrogen gas was led into the vigorously stirred solution at room temperature. It was worked up in the manner described in Example 6. The residue 3.3 grams had a rotary value $[\alpha]_D^{20} = -59.1°$ (c=2/H$_2$O), which corresponds to an optical yield of 88.6%.

In accordance with the NMR spectrum starting material was no longer present.

EXAMPLE 17

3.0 grams of α-benzamido cinnamic acid were dissolved in 50 ml of absolute ethanol. There were added 0.4 ml of the catalyst solution of Example 15 and the reaction mixture sucked into an evacuated 100 ml autoclave which had been rinsed several times with argon. It was pressured with 20 bars of hydrogen pressure. After 2 hours the theoretical amount of hydrogen was taken up. The N-benzoyl-(S)-phenylalanine freed from catalyst and solved showed a rotary value of $[\alpha]_D^{27} = -38.3°$ (c=1/CH$_3$OH), corresponding to an optical yield of 95% based on the known rotary value from the literature $[\alpha]_D^{27} = -40.3°$ (c=1.CH$_3$OH). The NMR spectrum no longer showed starting material.

EXAMPLE 18

3.25 grams of p-acetoxy-m-methoxy-α-acetamido-cinnamic acid were dissolved in 40 ml of absolute alcohol and treated with 0.5 ml of the catalyst solution of Example 15. The reaction mixture was sucked into a 100 ml autoclave. It was pressurized with 6.6 bars of hydrogen pressure. After 6.25 hours the reaction was ended. The p-acetoxy-m-methoxy-N-acetyl-(S)-phenylalanine, 3.2 grams, worked up in the customary manner (e.g., see Example 6) had a rotary value $[\alpha]_D^{27} = +35.8°$, corresponding to an optical yield of 88%, if the rotary value of the pure enantiomer of 40.7° (c=1/CH$_3$OH) is taken as a basis.

The NMR spectrum no longer showed starting material.

EXAMPLE 19

Production in situ of the catalyst cyclo-octadiene ((S)-1,2-bis-(diphenylphosphino)-3-methyl-butane)-Rhodium-acetylacetonate For the production of the catalyst solution there were dissolved in 10 ml of absolute ethanol at room temperature 0.2083 gram of the (S)-1,2-bis-(diphenylphosphino)-3-methyl-butane produced in Example 4 and 0.2970 gram of cyclooctadiene-rhodium-acetylacetonate.

EXAMPLE 20

3.5 grams of acetamido-acrylic acid together with 0.2 ml of the catalyst solution produced in Example 19 were dissolved in 75 ml of absolute ethanol in a 250 ml flask. Over a time span of 6.5 hours there was conducted hydrogen into the vigorously stirred solution at room temperature. It was worked up as described in Example 6. The N-acetyl-(R)-alanine, 3.4 grams, worked up as customary (e.g. see Example 6) had a rotary value $[\alpha]_D^{20} = +59.0°$ (c=2/H$_2$O), corresponding to an optical yield of 88.5%.

EXAMPLE 21

3.2 grams of α-benzamido-cinnamic acid were dissolved in 40 ml of absolute ethanol and treated with 0.3 ml of the catalyst solution produced in Example 19. The reaction mixture was sucked into a 100 ml autoclave. It was pressurized with 6 bars of hydrogen pressure. After taking up the theoretical amount of hydrogen it was worked up as customary (e.g. see Example 6). There were isolated 3.15 grams of N-benzoyl-(R)-phenylalanine having the rotary value of $[\alpha]_D^{27} = +38.6°$ (c=1/CH$_3$OH), corresponding to an optical yield of 95.8%.

The NMR spectrum no longer showed starting material.

The entire disclosure of German priority application No. P 3000445.6-42 is hereby incorporated by reference.

What is claimed is:
1. An optically active 1,2-bis-(diphenylphosphino)-compound of the formula
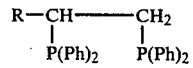
in which Ph is a phenyl group and R is isopropyl, isobutyl, sec.butyl or a benzyl group.
2. A compound according to claim 1 wherein R is an benzyl.
3. A compound according to claim 2 wherein R is isopropyl, isobutyl or sec. butyl.
4. A compound according to claim 3 wherein R is isopropyl.